United States Patent [19]
Zeng et al.

[11] Patent Number: 5,647,368
[45] Date of Patent: Jul. 15, 1997

[54] IMAGING SYSTEM FOR DETECTING DISEASED TISSUE USING NATIVE FLUORSECENCE IN THE GASTROINTESTINAL AND RESPIRATORY TRACT

[75] Inventors: Haishan Zeng; Richard W. Cline; Calum E. MacAulay; Bruno W. Jaggi, all of Vancouver, Canada

[73] Assignee: Xillix Technologies Corp., Richmond, Canada

[21] Appl. No.: 608,185

[22] Filed: Feb. 28, 1996

[51] Int. Cl.⁶ ...................................................... A61B 5/00
[52] U.S. Cl. ........................ 128/665; 128/664; 128/633; 128/634
[58] Field of Search .................................... 128/664, 665, 128/633, 634; 356/433, 435, 342, 343, 338, 432; 250/330–334, 461.2, 574–575, 358.1

[56] References Cited

U.S. PATENT DOCUMENTS

| | | |
|---|---|---|
| 4,473,841 | 9/1984 | Murakoshi et al. . |
| 4,541,438 | 9/1985 | Parker et al. . |
| 4,556,057 | 12/1985 | Hiruma et al. . |
| 4,718,417 | 1/1988 | Kittrell et al. . |
| 4,719,508 | 1/1988 | Sasaki et al. . |

(List continued on next page.)

FOREIGN PATENT DOCUMENTS

| | | |
|---|---|---|
| 0215772 | 3/1987 | European Pat. Off. . |
| 0512965A1 | 11/1992 | European Pat. Off. . |
| 2-22331 | of 1983 | Japan . |
| 2203831 | 10/1988 | United Kingdom . |
| 86/02730 | 5/1986 | WIPO . |
| 90/10219 | 9/1990 | WIPO . |
| 90/12536 | 11/1990 | WIPO . |
| 95/00171 | 3/1995 | WIPO . |

OTHER PUBLICATIONS

Alfano et al., "Fluorescence Spectra from Cancerous and Normal Human Breast and Lung Tissues," *IEEE Journal of Quantum Electronics*, vol. QE–23, No. 10, 1987, pp. 1806–1811.

Andersson–Engels et al., "Fluorescence Characteristics of Atherosclorotic Plaque and Malignant Tumors," *SPIE*, vol. 1426, 1991, pp. 31–43.

Andersson–Engels et al., "Tissue Diagnostics Using Laser–Induced Fluorescence," Ber Bunsenges, *Phys. Chem.*, vol. 93, 1989, pp. 335–342.

Coffey et al., "Evaluation of Visual Acuity During Laser Photoradiation Therapy of Cancer," *Lasers in Surgery and Medicine*, vol. 4, pp. 65–71.

(List continued on next page.)

*Primary Examiner*—Marvin M. Lateef
*Assistant Examiner*—Eleni Mantis Mercader
*Attorney, Agent, or Firm*—Christensen O'Connor Johnson and Kindness PLLC

[57] ABSTRACT

A system for detecting cancerous or precancerous lesions directs light produced from a mercury arc lamp into an illumination guide of an endoscope. Autofluorescence light produced by the tissue under examination is divided into red and green spectral bands by a dichroic mirror. Light in the red and green spectral band is applied to a pair of image intensified CCD cameras. The output of the camera that receives light in the red spectral band is coupled to a red video input of a color video monitor. Light produced by the camera that receives light in the green spectral band is coupled to the blue and green video inputs of the video monitor. The system produces a false color display, whereby healthy tissue appears cyan in color and cancerous or precancerous lesions appear reddish in color. The image displayed allows the operator to see the lesions within the context of the underlying tissue structures. The color contrast is adjustable to account for the autofluorescence property changes from patient to patient and from location to location.

13 Claims, 5 Drawing Sheets

U.S. PATENT DOCUMENTS

| | | |
|---|---|---|
| 4,768,513 | 9/1988 | Suzuki . |
| 4,773,097 | 9/1988 | Suzaki et al. . |
| 4,774,568 | 9/1988 | Matsuo . |
| 4,786,813 | 11/1988 | Svanberg et al. . |
| 4,805,597 | 2/1989 | Iwakoshi . |
| 4,821,117 | 4/1989 | Sekiguchi . |
| 4,827,908 | 5/1989 | Matsuo . |
| 4,852,579 | 8/1989 | Gilstad et al. . |
| 4,858,001 | 8/1989 | Milbank et al. . |
| 4,860,731 | 8/1989 | Matsuura . |
| 4,867,137 | 9/1989 | Takahashi . |
| 4,868,647 | 9/1989 | Uehara et al. . |
| 4,900,934 | 2/1990 | Peeters et al. ............... 250/461.2 |
| 4,930,516 | 6/1990 | Alfano et al. . |
| 4,938,205 | 7/1990 | Nudelman . |
| 4,957,114 | 9/1990 | Zeng et al. . |
| 4,993,404 | 2/1991 | Lane . |
| 4,998,972 | 3/1991 | Chin et al. . |
| 5,003,977 | 4/1991 | Suzuki et al. . |
| 5,042,494 | 8/1991 | Alfano . |
| 5,071,417 | 12/1991 | Sinofsky . |
| 5,078,150 | 1/1992 | Hara et al. . |
| 5,090,400 | 2/1992 | Saito . |
| 5,091,652 | 2/1992 | Mathies et al. . |
| 5,115,137 | 5/1992 | Andersson-Engels et al. . |
| 5,117,466 | 5/1992 | Buican et al. . |
| 5,125,404 | 6/1992 | Kittrell et al. . |
| 5,131,398 | 7/1992 | Alfano et al. . |
| 5,196,928 | 3/1993 | Karasawa et al. . |
| 5,318,023 | 6/1994 | Vari et al. . |
| 5,318,024 | 6/1994 | Kittrell et al. . |
| 5,377,676 | 1/1995 | Vari et al. . |
| 5,421,337 | 6/1995 | Richards-Kortum et al. . |
| 5,421,339 | 6/1995 | Ramanujam et al. . |
| 5,507,287 | 4/1996 | Palcic et al. ............... 128/633 |

OTHER PUBLICATIONS

Cothren et al., "Gastrointestinal Tissue Diagnosis by Laser-Induced Fluorescence Spectroscopy at Endoscopy," *Gastrointestinal Endoscopy*, vol. 36, No. 2, 1990, pp. 105–111.

Dougherty et al., "Cutaneous Phototoxic Occurences in Patients Receiving Photofrin," *Lasers in Surgery and Medicine*, vol. 10, 1990, pp. 485–488.

Hayata et al., "Fiberoptic Bronchoscopic Laser Photoradiation for Tumor Localization in Lung Cancer," *Chest*, vol. 82, 1982, pp. 10–14.

Hirano et al., "Photodynamic Cancer Diagnosis and Treatment System Consisting of Pulse Lasers and an Endoscopic Spectro-Image Analyzer," *Laser in Life Sciences*, vol. 3(1), 1989, pp. 1–18.

Hung et al., "Autofluorescence of Normal and Malignant Bronchial Tissue," *Lasers in Surgery and Medicine*, vol. 11, 1991, pp. 99–105.

Ikeda, "New Bronichial TV Endoscopy System," Elsevier Science Publishers B.V. Biomedical Press, 1988.

Kapadia et al., "Laser-Induced Fluorescence Spectroscopy of Human Colonic Mucosa," *Gastroenterology*, vol. 99, 1990, pp. 150–157.

Kato et al., "Early Detection of Lung Cancer by Means of Hematoporphyrin Derivative Fluorescence and Laser Photoradiation," *Clinics in Chest Medicine*, vol. 6, No. 2, 1985, pp. 237–253.

Kato et al., "Photodynamic Diagnosis in Respiratory Tract Malignancy Using an Excimer Dye Laser System", *Journal of Photochemistry and Photobiology*, B. Biology, vol. 6, 1990, pp. 189–196.

Lam et al., "Fluorescence Detection," *Advances in the Diagnosis and Therapy of Lung Cancer*, Blackwell Scientific Publications Inc.

Lam et al., "Fluorescence Imaging of Early Lung Cancer," *IEEE Eng. Med. Biology*, vol. 12, 1990.

Lam et al., "Detection of Lung Cancer by Ratio Fluorometry With and Without Photofrin II," *SPIE Proc.* vol. 1201, 1990, pp. 561–568.

Lam et al., "Detection of Early Lung Cancer Using Low Dose Photofrin II", *Chest*, vol. 97, 1990, pp. 333–337.

Lam et al., "Mechanism of Detection of Early Lung Cancer by Ratio Fluorometry," *Lasers in Life Sciences*, vol. 4(2), 1991, pp. 67–73.

Montan et al., "Multicolor Imaging and Contrast Enhancement in Cancer-Tumor Localization Using Laser-Induced Fluorescence in Hematoporphyrin-derivative-bearing Tissue," *Optics Letters*, vol. 10(2), 1985, pp. 56–58.

Mullooly et al., "Dihematoporphyrin Ether-Induced Photosensitivity in Laryngeal Papilloma Patients," *Lasers in Surgery and Medicine*, vol. 10, 1990, pp. 349–356.

Palcic et al., "Development of a Lung Imaging Fluorescence Endoscope," Proceedings of the 12th Annual Int'l Conference of the IEEE Engineering in Medicine and Biology Society, vol. 12, No. 1, 1990.

Palcic et al., "The Importance of Image Quality for Computing Texture Features in Biomedical Specimens," *SPIE Proc.*, vol. 1205, 1990, pp. 155–162.

Palcic et al. "Lung Imaging Fluorescence Endoscope: A Device for Detection of Occult Lung Cancer," *Medical Design and Material*, 1991.

Palcic et al., "Lung Imaging Fluorescence Endoscope: Developement and Experimental Prototype," *SPIE*, vol. 1448, 1991, pp. 113–117.

Palcic et al., "Detection and Localization of Early Lung Cancer by Imaging Techniques," *Chest*, vol. 99, 1991, pp. 742–743.

Peak et al., "DNA-to-Protein Crosslinks and Backbone Breaks Caused by FAR-and NEAR-Ultraviolet and Visible Light Radiations in Mammalian Cells," Mechanism of DNA Damage and Repair, Implications for Carcinogenesis and Risk Assessment, 1986, pp. 193–202.

Profio et al., "Digital Background Subtraction for Fluorescence Imaging," *Medical Physics*, vol. 13(5), 1988, pp. 717–727.

Profio et al., "Endoscopic Fluorescence Detection of Early Lung Cancer," *SPIE*, vol. 1426, 1991, pp. 44–46.

Profio et al., "Fluorometer for Endoscopic Diagnosis of Tumors," *Medical Physics*, vol. 11(4), 1984, pp. 516–520.

Profio et al., "Laser Fluorescence Bronchoscope for Localization of Occult Lung Tumors," *Medical Physics*, vol. 6, 1979, pp. 523–525.

Rava et al., "Early Detection of Dysplasia in Colon and Bladder Tissue Using Laser Induced Fluorescence," *SPIE*, vol. 1426, 1991, pp. 68–78.

Razum et al., "Skin Photosensitivity: Duration and Intensity Following Intravenous Hematoporphyrin Derivatives, $H_pD$ and DHE, " *Photochemistry and Photobiology*, vol. 46, No. 5, 1987, pp. 925–928.

Richards-Kortum et al., "Spectroscopic Diagnosis of Colonic Dysplasia: Spectroscopic Analysis," *Biochemistry and Photobiology*, vol. 53, No. 6, 1991, pp. 777–786.

Tang et al., "Spectroscopic Differences Between Human Cancer and Normal Lung and Breast Tissues," *Lasers in Surgery and Medicine,* vol. 9, 1989, pp. 290–295.

Wagnieres et al., "Photodetection of Early Cancer by Laser Induced Fluorescence of a Tumor–Selective Dye: Apparatus Design and Realization," *SPIE Proc.,* vol. 1203, 1990, pp. 43–52.

IMAGING SYSTEM FOR DETECTING DISEASED TISSUE USING NATIVE FLUORSECENCE IN THE GASTROINTESTINAL AND RESPIRATORY TRACT

FIELD OF THE INVENTION

The present invention relates to cancer detection systems, and in particular to cancer detection systems that measure the native fluorescence response of normal, precancerous and cancerous tissue.

BACKGROUND OF THE INVENTION

One of the leading causes of death among humans is cancer. Despite the high mortality rates, many cancers can be cured if detected and treated early. To that end, considerable effort has been devoted to the design and development of screening systems that aid the physician in the detection of the presence of early stage cancerous or precancerous tissue.

One of the more recent methods for detection and treatment of cancers in internal body cavities is fluorescence imaging. This imaging mode provides different information than the conventionally used reflectance imaging mode. In both imaging modes, the physician inserts an endoscope or fiber optic bundle into the body cavity which conducts illumination into the cavity from a light source. In reflectance imaging, the light source is typically white light whereas in fluorescence, a specific excitation wavelength(s) is used. The reflectance or fluorescence image is captured by the imaging fiber bundle of the endoscope and viewed by the physician through the ocular of the endoscope. Alternatively, a camera can be attached to the ocular so that the image can be displayed on a monitor.

In prior art fluorescence imaging systems, a physician typically prepares a patient by administering a photosensitive drug that binds to cancerous tissue. The photosensitive drugs cause the cancerous tissue to contrast with the surrounding tissue, thereby allowing the physician to visually detect the presence of cancer. The problem with the use of photosensitive drugs to detect cancer is that most drugs have significant side effects. The most serious side effect is that the patients become hyper sun sensitive while the drugs are active. Therefore, patients who receive these drugs must be kept in darkened rooms for several days after the administration of the drugs. This method of cancer detection is therefore not suited for screening applications where it is desired to test as many patients as possible in the least amount of time.

Another cancer detection method based on fluorescence imaging that eliminates the need to administer photosensitive drugs is based on the fact that cancerous or precancerous tissue responds differently to applied light than does normal tissue. When monochromatic light is applied to living tissue, a portion of the absorbed light will be re-emitted at different wavelengths in a process termed autofluorescence (also referred to as native fluorescence). If blue or ultraviolet light is applied to living tissue, the intensity or number of autofluorescence photons released by the abnormal tissue in the green portion of the visible light spectrum differs relative to the intensity or number of photons released by healthy tissue. In the red region of the visible light spectrum, the number of photons released by the healthy and abnormal tissue are closer to being similar.

Examples of prior art systems which utilize the difference in fluorescence and autofluorescence intensity to detect the presence of cancer cells include U.S. Pat. No. 4,786,813 to Svanberg et al.; U.S. Pat. No. 4,930,516 ('516) to Alfano et al.; U.S. Pat. No. 5,042,494 ('494) to Alfano; U.K. Patent Application No. 2,203,831, by Zeng Kun; U.S. Pat. No. 5,131,398 ('398) to Alfano et al.; and PCT application No. WZ 90/10219 by Andersson-Engles.

The systems described in each of these patents generally fall into two categories in order to discriminate between cancerous and non-cancerous cells. The first category one utilizes single point, narrow band spectroscopy measurements to detect cancerous tissue, while the second utilizes broad band imaging systems. Examples of the systems in the first category are the Alfano patents, '516, '494 and '398, which describe single point measurement systems. These systems use a ratiometric comparison of the narrow band intensity of autofluorescence light produced by healthy and suspect tissue, as well as a detection of a change in spectral peaks (i.e., a shift towards the blue) to indicate the presence of cancerous cells. However, these narrow band intensity measurements and the associated discrimination algorithm is based on an autofluorescence spectra derived from in vitro measurements of rat tumors that have not been found to be applicable to cancer in humans. The Zeng system simply looks for a change in the spectral envelope of the autofluorescence light to detect malignant tissue. However, this method has not proven sufficiently reliable to identify suspicious tissue in different patients due to changes in the amount of autofluoresence light produced as the probe is moved from one location to another or one patient to another.

Examples of the second category are illustrated by the Svanberg et al. and Andersson-Engles patents, which disclose systems for producing images of diseased tissue. The fluorescence or autofluorescence light produced by the tissue is divided into four beams that are filtered with a broadband filter before being applied to an intensified CCD camera. The output of the intensified CCD camera is used to compute ratios of the intensity of the four broad spectral bands. The ratio calculations are then displayed, typically as pseudo colors, on a monitor so that a physician can visually detect the presence of cancerous lesions. However, the calculation of ratios or the requirement for image processing is not desirable in a medical diagnostic aid system because the physician loses information that is, in our experience, necessary for diagnostic judgment. Such information is only retained by presenting the physician with a view of the tissue directly and not a mathematical representation of the tissue.

A new development which leads to an apparatus for detecting the presence of cancerous tissue based on the differences in autofluorescence light is disclosed in our copending U.S. patent applications Ser. Nos. 08/428,494 ('494), now U.S. Pat. No. 5,507,287 and 08/218,662 ('662), which are herein incorporated by reference. While the systems disclosed in the '494 and '662 applications constitute a significant advance in the field of cancer imaging, improvements can be made. For example, these systems require complex laser systems in order to produce the fluorescence excitation light. Although it is possible to use a relatively small ion laser, such as the HeCd laser, this has the disadvantage that the illumination power is not great enough for the examination of large cavity organs such as the colon and stomach. Furthermore, if fluorescence imaging is used together with white light reflectance imaging, an additional light source has to be used. Additionally, there are currently no cancer imaging systems that are designed to compensate for the changes of autofluorescence properties from patient to patient, from organ to organ, and from location to location. Finally, the manner in which cancerous or precancerous tissue is displayed does not take optimal advantage of the perceived color discrimination of the human eye.

The present invention is directed to address the problems of prior art cancer imaging systems and to improve the systems disclosed in the '494 and '662 applications in order to facilitate the detection of cancerous or precancerous tissue in the respiratory and gastrointestinal tracts.

SUMMARY OF THE INVENTION

The present invention is an imaging system for detecting the presence of cancerous or precancerous lesions in vivo. A light source produces blue excitation light that is directed into an illumination guide of a fiber optic endoscope in order to illuminate a portion of tissue to be examined. The endoscope returns some reflected excitation light as well as autofluorescence light produced by the tissue under examination. Light received from the endoscope, through the imaging fiber bundle, is divided into two beams by a dichroic mirror. The first beam comprises autofluorescence light in the green portion of the visible light spectrum as well as any reflected blue excitation light. The second beam comprises autofluorescence light in the red portion of the spectrum. Light in the two beams is filtered and applied to a pair of image intensified CCD cameras. Real time images (i.e., 30 frames/s), produced by the CCD cameras, are applied to the red, green and blue color inputs of a color video monitor. Still images can be captured from the real time images and stored by means of a frame grabber in a computer.

The blue and green color inputs of the video monitor are connected to receive the images produced by the camera that detects green autofluorescence light, while the red color input of the color video monitor is connected to receive the image produced by the camera that detects the red autofluorescence light. The video monitor produces a display whereby normal tissue appears as approximately cyan in color, while potentially cancerous tissue appears reddish in color. It turns out that the perceived colors on the monitor represent the ratio of the two acquisition channels. This is an important aspect of the present invention since the ratio is displayed without calculations or digital image processing but by simply mixing the three color channels.

A further aspect of the invention is a pair of controls that allow a physician to adjust the brightness and color contrast of the video display image by adjusting the gain of the red and green intensified CCD cameras in a specific proportion to compensate for the changes in autofluorescence from patient to patient, from organ to organ, and from location to location.

Another aspect of the invention is an improvement to the excitation light source. A mercury arc lamp is used to produce the blue excitation light at the strong atomic line of 436 nanometers. Light from the arc lamp is gathered by an elliptical mirror and filtered by a dichroic mirror and a bandpass filter before it is directed into the illumination guide of the endoscope. This filtered light source gives high illumination power and is inexpensive to manufacture and is relatively easy to maintain.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a system for detecting cancerous or precancerous tissues using autofluorescence images that does not require the use of tumor enhancing drugs or intensive image processing.

Figure 1:
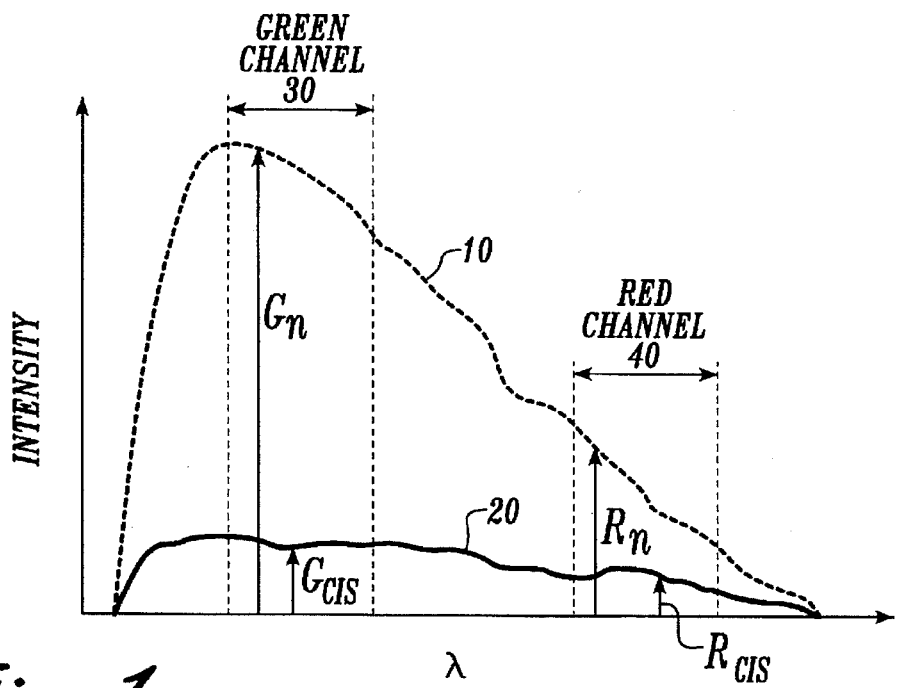
FIG. 1 is a graph showing the difference in autofluorescence intensity between normal and cancerous tissue.

FIG. 1 is a graph showing the differences in autofluorescence light intensity for normal and cancerous or precancerous tissue in humans. As indicated above, when blue excitation light is shined on tissue, some of the light will be absorbed and reemitted as autofluorescence light. The autofluorescence light has an intensity and spectral shape that is indicative of whether the tissue is normal or diseased. A spectral curve 10 represents the response of normal, healthy tissue, while a spectral curve 20 represents the response of tissue that is cancerous or precancerous. As can be seen, there is a significant difference in the intensity of the two curves in a green channel 30, while the differences between the healthy and abnormal tissue in a red channel 40 is small.

The magnitude of the curves 10 and 20 shown in FIG. 1 not only vary with wavelength, but also with the distance between a probe and the tissue under examination as well as the intensity of the light source. Therefore, in a practical sense it is not possible to determine whether tissue is cancerous by simply detecting the magnitude of the autofluorescence light in the green channel. However, the ratios of the autofluorescence light intensities taken at two different wavelengths remain constant despite variations in the distance of the fiber optic probe to the tissue and the angle of the probe to the tissue. This is true since the intensities of the green and red channel change proportionally for the same kind of tissue. That is, the intensity of red autofluorescence light for normal tissue $R_n$ divided by the intensity of the green autofluorescence light for normal tissue $G_n$ remains substantially constant despite variations in the distance and angle of the tip of the endoscope to the tissue under consideration. Similarly, the ratio of the intensity of the red autofluorescence light $R_{CIS}$ (CIS for carcinoma in situ) divided by the intensity of the green autofluorescence light $G_{CIS}$ remains substantially constant despite variations in the position and orientation of the endoscope.

For healthy tissue, the inventors have found that the ratio of the response of the red channel to the green channel is approximately 0.54 for colon tissue and 0.16 for lung tissue, while for carcinoma in situ, the ratio of the red to green channel is approximately 1.6 for colon tissue and 0.6 for lung tissue. These values are given as examples only and they are highly dependent on the system, i.e., the spectral response of the imaging system. However, by calculating or by representing the ratio of the red channel autofluorescence light and the green channel autofluorescence light, a determination can be made whether the tissue under consideration is healthy or potentially cancerous when interpreted along with the contextual information of the image.

Figure 2:
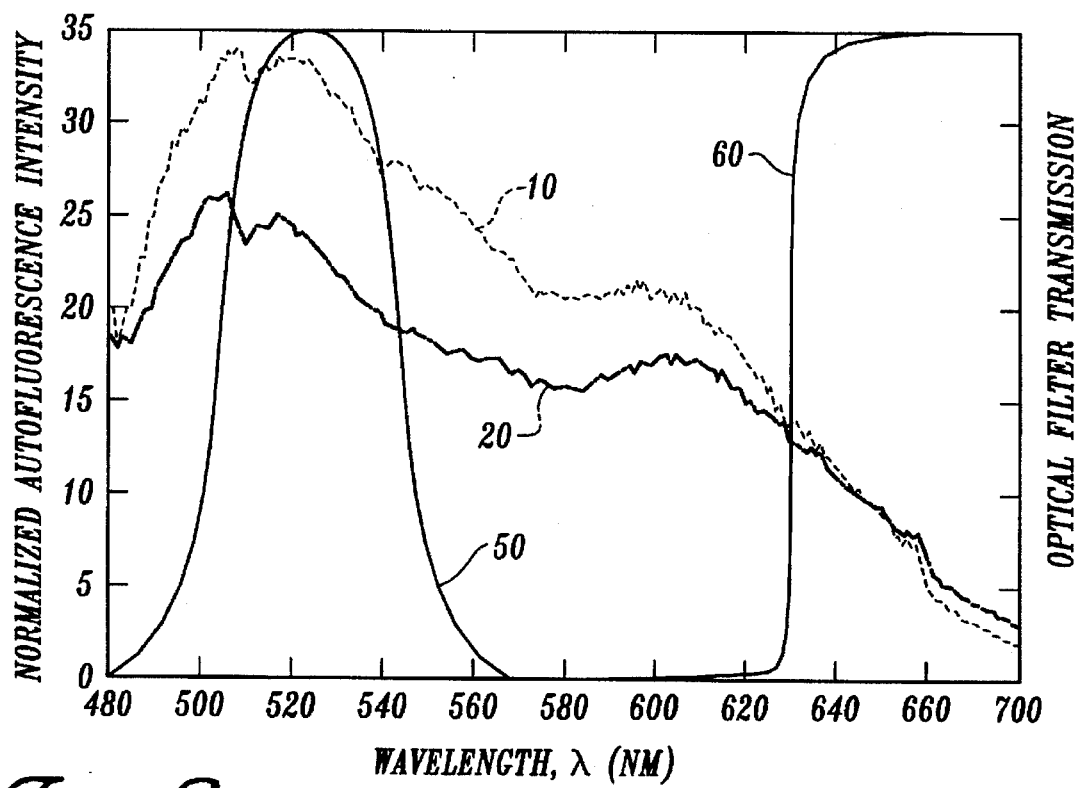
FIG. 2 is a graph showing the difference in autofluorescence spectral shape between normal and cancerous tissue in the spectral bands utilized by the present invention.

FIG. 2 shows the range of wavelengths used by the present invention to determine whether tissue is potentially cancerous or precancerous. The red channel is limited to wavelengths longer than 630 nanometers, while the green channel comprises wavelengths extending from approximately 490 to 560 nanometers. To demonstrate that the spectral curves are different not only in intensity but also in shape, the areas in the red band have been normalized so that, in this part of the spectrum, the ratio of the normal and cancerous tissue is one. This normalization still results in a significant difference in the green band. Therefore, the ratio or a representation of the ratio will discriminate between normal and cancerous tissue. By simultaneously displaying the autofluorescence light received in each of these bands as a color image, the present invention allows a physician to determine whether the tissue under consideration is potentially cancerous or precancerous.

Figure 3:
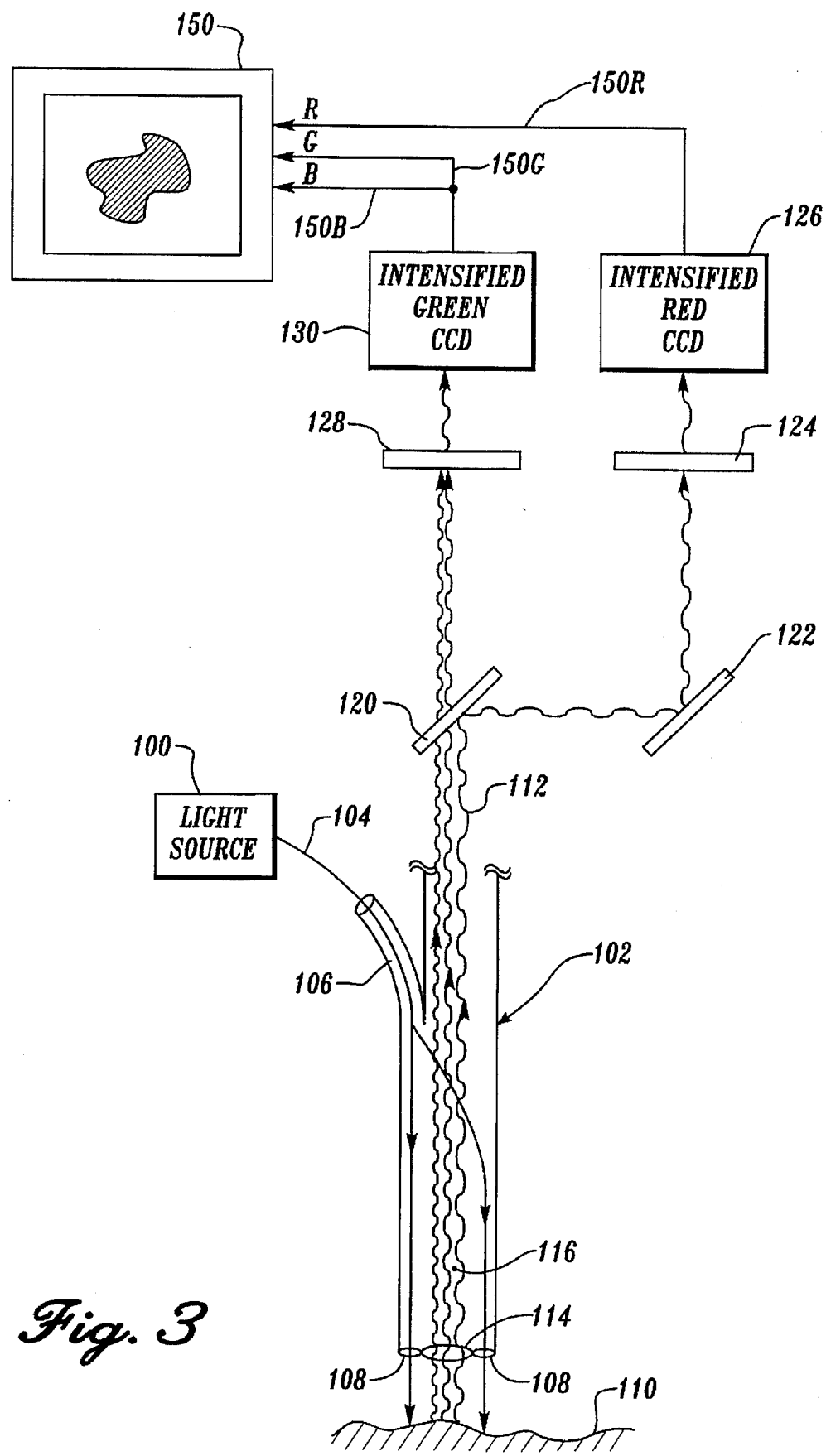
FIG. 3 is a block diagram of a cancer detection system according to the present invention.

Turning now to FIG. 3, the endoscope autofluorescence imaging system of the present invention includes an excitation light source 100 and a fiber optic endoscope 102, which may be a gastroscope, duodenoscope, choledochoscope, bronchoscope or colonoscope depending on the type of tissue to be examined. For example, the endoscope may be an Olympus BF-20D for the respiratory tract, an Olympus GIF-XQ30 for the esophagus and stomach and an Olympus CF-30L for the rectum and colon.

The light source 100 produces blue excitation light 104 which is fed through the incoherent illumination guide 106 of the fiber optic endoscope. The excitation light is focused by an outer lens 108 that is disposed at the distal end of the endoscope. When the endoscope is inserted into a body cavity by a physician, the blue excitation light illuminates a portion of tissue 110 that is to be examined. The tissue is excited by the blue light and emits photons (autofluorescence light) 112 having a longer wavelength in the visible portion of the light spectrum. The autofluorescence light emitted by the tissue along with some reflected blue excitation light is gathered by a lens 114 at the distal end of the endoscope and channeled through an imaging guide portion 116 of the endoscope through a number of conventional imaging lenses (not shown).

After exiting the endoscope, autofluorescence light is applied to a dichroic mirror 120. The dichroic mirror 120 has a cutoff wavelength between 565 and 575 nanometers. The dichroic mirror divides the autofluorescence light from the imaging guide into two spectral bands. The autofluorescence light having wavelengths longer than the cutoff wavelength of the dichroic mirror 120 is directed toward a reflection mirror 122 that directs the autofluorescence light into a filter 124. The filter 124 is positioned in front of a red channel, image intensified CCD camera 126. Autofluorescence light having wavelengths less than the cutoff wavelength of the dichroic mirror 120 passes through the dichroic mirror toward a filter 128 that is positioned in front of a second image intensified, green channel CCD camera 130.

By separating the autofluorescence light gathered by the endoscope into the two spectral bands, virtually all photons having wavelengths in the red portion of the spectrum are supplied to the CCD camera 126 while virtually all photons having wavelengths in the green portion of the spectrum are applied to the CCD camera 130. As shown in FIG. 1, the intensity of the red autofluorescence wavelength band that is applied to the camera 126 is substantially the same for normal tissue and abnormal tissue. However, the intensity of the green autofluorescence wavelength band applied to the camera 130 is substantially different for normal and abnormal tissue.

As will be described in further detail below, the images produced by both CCD cameras 126 and 130 are combined on a color video monitor 150 that allows any abnormal tissue to be easily identified. Because a high power blue excitation light is employed and all the photons in the spectral bands are applied to the image intensified CCD cameras 126 and 130, the images produced by the cameras 126 and 130 are bright enough to distinguish between normal and abnormal tissue, even in the larger organs such as in the gastrointestinal tract, without the need for tumor enhancing photosensitive drugs.

Figure 4:
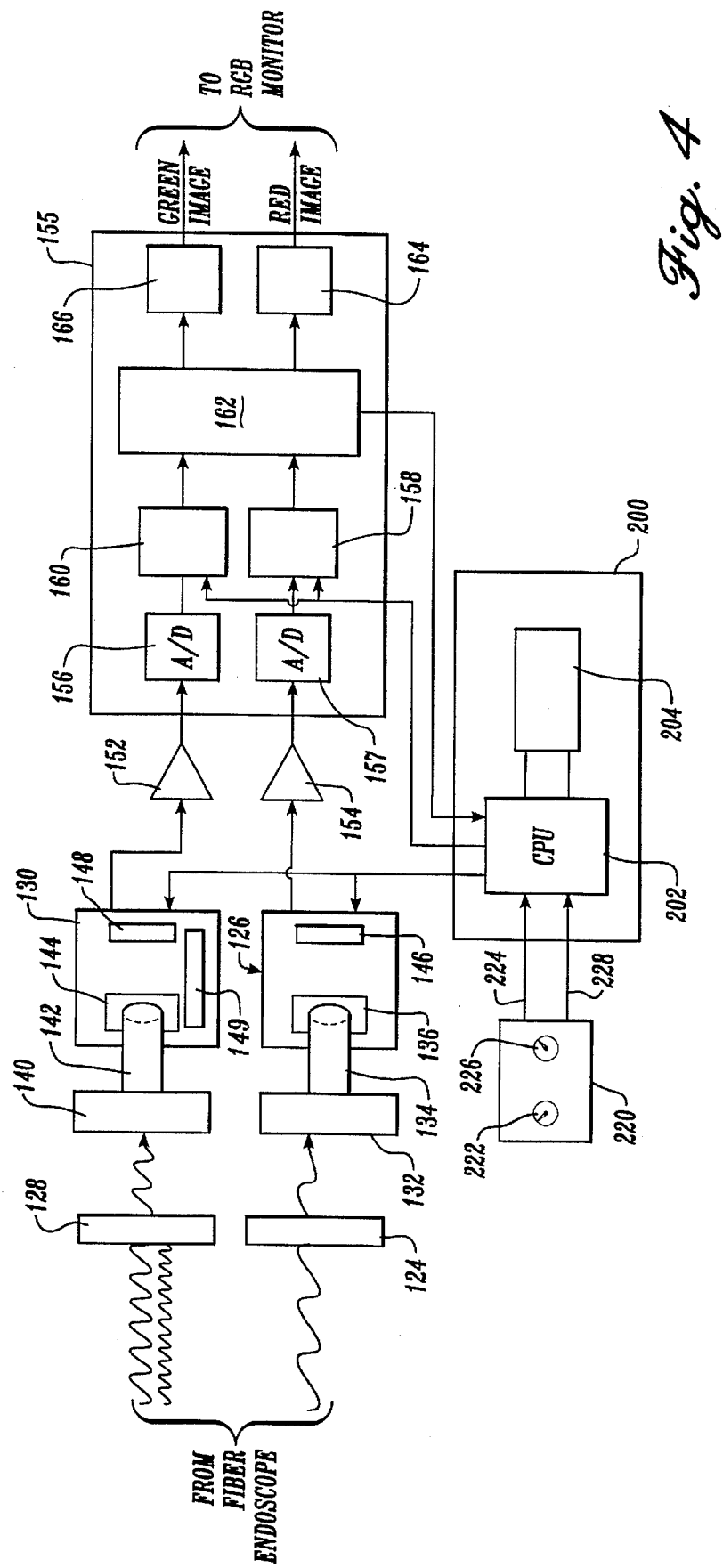
FIG. 4 is a block diagram of the image acquisition/processing units used with the cancer detection system of the present invention.

FIG. 4 is a more detailed block diagram of the imaging portion of the cancer detection system according to the present invention. After the autofluorescence light 112 is either reflected by or passes through the dichroic mirror 120 (FIG. 3), the light is directed to the filters 124 and 128. The filter 124 is a long pass filter that blocks light having wavelengths less than 630 nanometers. After passing through the long pass filter 124, the red autofluorescence light is directed onto the surface of a GEN II image intensifier 132 such as a DEP XX 1700 manufactured by Delft Instruments. The output of the image intensifier 132 is coupled through a fiber optic bundle 134 to the surface of a CCD image sensor 136 within the CCD camera 126.

The green autofluorescence light passes through a bandpass filter 128 that removes any blue excitation light that may have been reflected off the surface of the tissue 110. In the present embodiment of the invention, the bandpass filter 128 removes light having wavelengths less than 490 nanometers or greater than 560 nanometers. The out of band attenuation of the filters 124 and 128 must be sufficient to ensure that virtually all of the reflected blue excitation light is blocked from reaching the CCD cameras. After passing through the filter 128, the green autofluorescence light is directed to a GEN II image intensifier 140. The output of the image intensifier 140 is coupled via a fiber optic bundle 142 to the surface of a CCD image sensor 144 within the green CCD camera 130. A genlock 149 within the camera 130 maintains the synchronization of the red CCD camera 126 to the green CCD camera 130.

The analog output signals of the red and green image intensified CCD cameras 126 and 130 are fed to a pair of amplifiers 152, 154. The output of the amplifiers is fed into a video image processing board 155 that is part of a controlling computer 200. The controlling computer 200 includes an Intel 486/100 MHz CPU 202 and 16 MB of internal memory 204. However, other high speed digital computers could also be used.

The video image processing board 155 includes a pair of analog-to-digital converters 156, 157, that receive the amplified video signals from the red and green CCD cameras, respectively. The analog-to-digital converters convert the analog video signals into a corresponding digital format. After being digitized, a pair of look up tables 158 and 160 are used to modify the relative gain of the digital video signals in a manner that will be described below. For each discrete value of the digital video signal, the CPU 202 reads up a corresponding digital value having the correct relative gain from the look up tables. The values of the digitized video signals read from the look up tables 158, 160, that are part of a random access memory 162 where they can be retrieved by the central processing unit for analysis at a later time.

To display the image signals in real time, the digital video signals are continuously retrieved from the random access memory 162 and reconverted into an analog format by a pair of digital-to-analog converters 164 and 166. The two converters correspond to the green and red channel images. The outputs of the digital to analog converters 164, 166, are applied directly to the red, green and blue inputs of the color monitor 150 shown in FIG. 3. This means that the video signal from the green CCD camera 130 is coupled to a green input 150G of the color monitor as well as a blue input 150B. A red input 150R of the color monitor receives the video signal from the red CCD camera 126.

The color video monitor 150 receives the video signals and produces a color image, whereby the healthy tissue is approximately cyan in color and any abnormal or potentially cancerous tissue appears reddish in color and is therefore easily identifiable by a trained physician.

The direct coupling of the video signals from the video input/output board 152 and 154 through the video image processing board 155 to the color video monitor 150 is accomplished without any significant digital signal processing other than a minor change in the gain as will be described below. This allows a physician to view as true a representation of the data from the intensified CCD cameras as possible. In other words, the structure (e.g., contrast and texture) of the image are maintained. Therefore, the physician is able to consider subtleties in the video image that may otherwise be removed or masked as a result of any digital image processing that takes place before the image is displayed. The two autofluorescence image signals produced by the CCD cameras are representative of the true autofluorescence image of the tissue in the respective wavelength bands, allowing lesions to be seen at video rates within their context. This aspect is essential for the physician to recognize potential lesions which he/she can then biopsy through the biopsy channel of the endoscope for pathology confirmation.

The fluorescence imaging system of the present invention is unique in that it does not perform calculations to compensate for distance and angle effects of the endoscope with respect to the tissue under examination. Instead, the images from the red and green cameras are superimposed upon each other and displayed as distinct colors. This allows the physician to interpret the image using the visual experience they have acquired over their lifetime. In addition, the system circumvents the problem of an algorithm making a clinical decision as to what tissue may or may not be cancerous as well as allows the tissue to be observed in real time.

The inventors have found that the autofluorescence properties of tissue change from patient to patient, from organ to organ, and from location to location. Therefore, the present invention provides a set of controls 220 that allow the physician to adjust the "brightness" and "color balance" of the color video image produced. The controls 220 can be realized by hardware or software control of the camera gain.

The brightness of the displayed image is related to the gain of both the red and green channels while the color balance is related to the relative gain of the green and red channels. In the presently preferred embodiment of the invention, the gain of the red channel camera 126 is related to the gain of the green channel camera 130 according to the equation:

$$R_{(G)} = aG^2 + bG + c \quad (1)$$

where R is the gain of the red channel image intensifier and G is the gain of the green channel image intensifier, and a, b and c are constant. As will be appreciated, the particular values selected for the constants a, b and c depend on the type of intensified CCD camera used, the intensity of the light source, the properties of the tissue and the human eye's ability to perceive color. However, for the system described above, the inventors have found that the constant "a" should be selected in the range of 0.0 to 0.1, "b" should be in the range of 0.5 to 1.5, and "c" should be selected from the range of 0.0 to 0.5.

The constant "c" provides for an offset in color between the two channels while the linear term "b" ensures that as the overall brightness is changed, the gain of both the green and red channels is related. The quadratic term "a" provides a second order connection to ensure that the perceived color on the monitor remains the same despite variations to the overall brightness of the display. However, in the present embodiment of the invention, the "a" term is set to zero.

To adjust the brightness of the image displayed on the monitor, the physician adjusts the position of a knob 222 which adjusts the gain of the green channel. Movement of this knob 222 produces signals on a lead 224 that are read by the CPU 202. The CPU 202 then adjusts the numbers stored in the look up tables 158 and 160 according to Equation 1 without changing the values of the constants a, b and c. Alternatively, the CPU can adjust the gain of the red and green intensified CCD cameras by supplying gain signals from the CPU to a pair of gain control boards 146, 148, which control the high voltage of the image intensifiers 132, 140. As will be appreciated, as the gain of the green channel is increased or decreased, the gain of the red channel is increased or decreased proportionally.

To adjust the color balance of the image, the physician adjusts the position of a contrast knob 226. Movement of the knob 226 produces signals on a lead 228 that are read by the CPU 202. The CPU then adjusts the multiplier b that relates the gain of the red channel to the gain of the green channel. In the present embodiment of the invention, the constant "b" is varied linearly in the range described above as the contrast control knob 226 is moved between its minimum and maximum positions. The CPU then calculates a gain of the red channel by recalculating the values stored in the look up table 158 or adjusts the gain of the red channel image intensifier camera 132 by supplying a new gain signal to the gain control board 146.

In practice, the physician adjusts the brightness control knob 222 until an image of sufficient intensity of the tissue is produced on the video monitor 150. If the physician believes he or she is viewing a malignant lesion, the position of the color balance knob 226 is adjusted until the entire video image appears red. The color balance knob can be readjusted until no red is apparent in the background of the video image. If the area of interest still appears reddish in color, the physician can have greater certainty that the red portion of the video image is a cancerous or precancerous lesion. The color balance control knob 226 can also be adjusted so that the displayed color is what the physician wants to see, thereby giving the physician some flexibility in setting the display to be something that is easier for the individual physician to interpret.

As indicated above, the present invention displays tissue on the color monitor as a color that is not dependent upon the position or orientation of the endoscope with respect to the tissue under examination. The rationale as to why this is true for the present invention is stated below.

In general, any RGB color monitor can be modeled according to the following equation:

$$\begin{bmatrix} X \\ Y \\ Z \end{bmatrix} = \begin{bmatrix} a_{11} & a_{12} & a_{13} \\ a_{21} & a_{22} & a_{23} \\ a_{31} & a_{32} & a_{33} \end{bmatrix} \begin{bmatrix} R \\ G \\ B \end{bmatrix} \quad (2)$$

The values R, G and B are the magnitudes of the video signals applied to the color inputs of the monitor and the 3×3 matrix comprises a series of fixed coefficients that are primarily determined by the phosphor used on the monitor. The values, X, Y and Z are referred to as tristimulus values.

Figure 5:
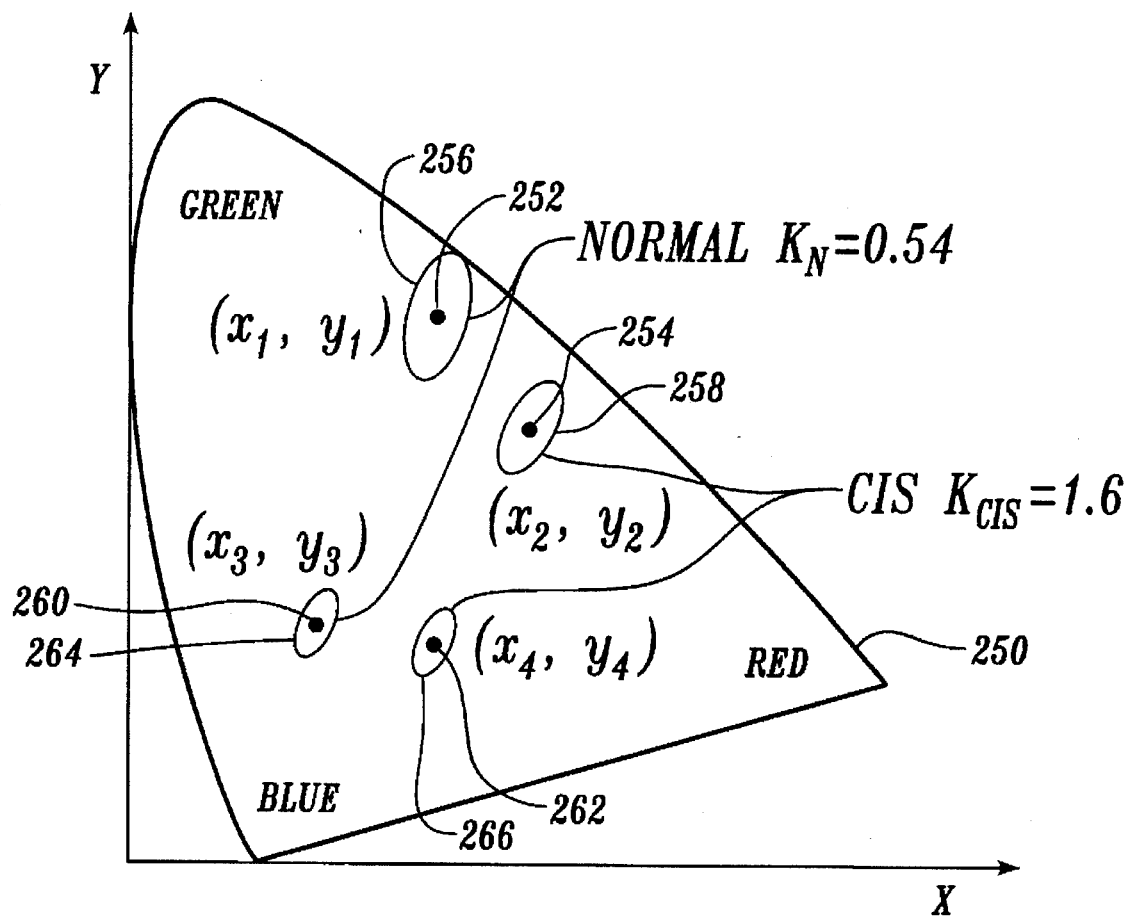
FIG. 5 is a chromaticity diagram showing how the perceived color for normal and cancerous tissue are displayed by the cancer detection system of the present invention.

Every color that can be displayed on the monitor can be represented as a pair of color coordinates x, y, on a chromaticity diagram 250 as shown in FIG. 5. This is a widely used conventional diagram used to represent colors that can be displayed on a video monitor. The coordinates x and y are related to the tristimulus values by the equations:

$$x = \frac{X}{X+Y+Z} \quad (3)$$

$$y = \frac{Y}{X+Y+Z} \quad (4)$$

The Television Engineering Handbook by K. Blair Benson (McGraw Hill, 1992) is a typical reference where these equations and definition of the chromaticity diagram can be found.

Since, for the present invention, the green signal G is fed into the blue channel, G=B, one can expand Equations 2 and 3 arriving at the following:

$$x = \frac{a_{11}R + (a_{12}+a_{13})G}{(a_{11}+a_{21}+a_{31})R + (a_{12}+a_{22}+a_{23}+a_{13}+a_{32}+a_{33})G} \quad (5)$$

Similarly, expanding Equations 2 and 4, gives the following:

$$y = \frac{a_{21}R + (a_{22}+a_{23})G}{(a_{11}+a_{21}+a_{31})R + (a_{12}+a_{22}+a_{23}+a_{13}+a_{32}+a_{33})G} \quad (6)$$

For the cancer detection systems of the present invention, it has been determined that the ratio of the red to green autofluorescence intensity remains the same for a given tissue regardless of the intensity of the excitation light, orientation of the probe, or distance of the probe to the tissue under examination. If the R/G is a constant, i.e., R/G=k, x of Equation 5 and y of Equation 6 will remain constant. Hence, the color shown on the monitor 150 will be constant regardless of how the probe is positioned within the patient. The only time the ratio between the red and green autofluorescence light changes and hence the only time the color on the video monitor changes is when the tissue under examination is potentially cancerous (since in that case, the ratio R/G changes due to the different spectral response). Therefore, a physician needs only to look for variations in the color of the display to detect potentially cancerous lesions.

It has been determined that for the cancer detection system described above, the ratio of the red to green autofluorescence light for healthy colon tissue is approximately 0.54. When the color coordinates x and y, of the chromaticity graph, are computed and plotted for Equations 3 and 4 given that for a constant R/G ratio of 0.54, as shown in FIG. 5, it results in a point 252 having coordinates $x_1$, $y_1$ with a greenish hue. Similarly, it has been determined that the ratio of the red to green autofluorescence light for potentially cancerous colon tissue is approximately 1.6 which, when plotted, results in a point 254 having coordinates $x_2$, $y_2$ with a red-brown hue.

About each point on the chromaticity graph lies an area 256, 258, 264 and 266 about which the human eye cannot perceive changes in color. It has further been determined that these areas tend to decrease in size as the value of x, y decreases, i.e., the colors shown in the blue to red region of the chromaticity diagram. By feeding the green autofluorescence signal into both the blue and green inputs of the color monitor, the position of point 252 moves to a point 260, having coordinates $x_3$, $y_3$, in the blue region of the chromaticity graph. Similarly, the point 254 is moved to a point 262, having coordinates $x_4$, $y_4$, near the red region of the graph. Because the colors displayed are in an area where the human eye is more perceptive of slight color changes, a physician is more easily able to detect slight variations in color and, hence, can more readily detect potentially cancerous tissue.

To display the R/G ratio as a color is an important part of the present invention. In the prior art it is difficult to calculate and display the ratio in real time video rates of 30 frames per second. In addition, the display of a calculated ratio does not provide contextual information. Contextual information is, in our experience, essential to allow a physician to determine whether a suspicious lesion requires a biopsy or whether or not an artifact is observed (e.g., blood). The color display system of the present invention is fast because no calculations are performed and the resulting image retains the tissue contextual information.

Figure 6:
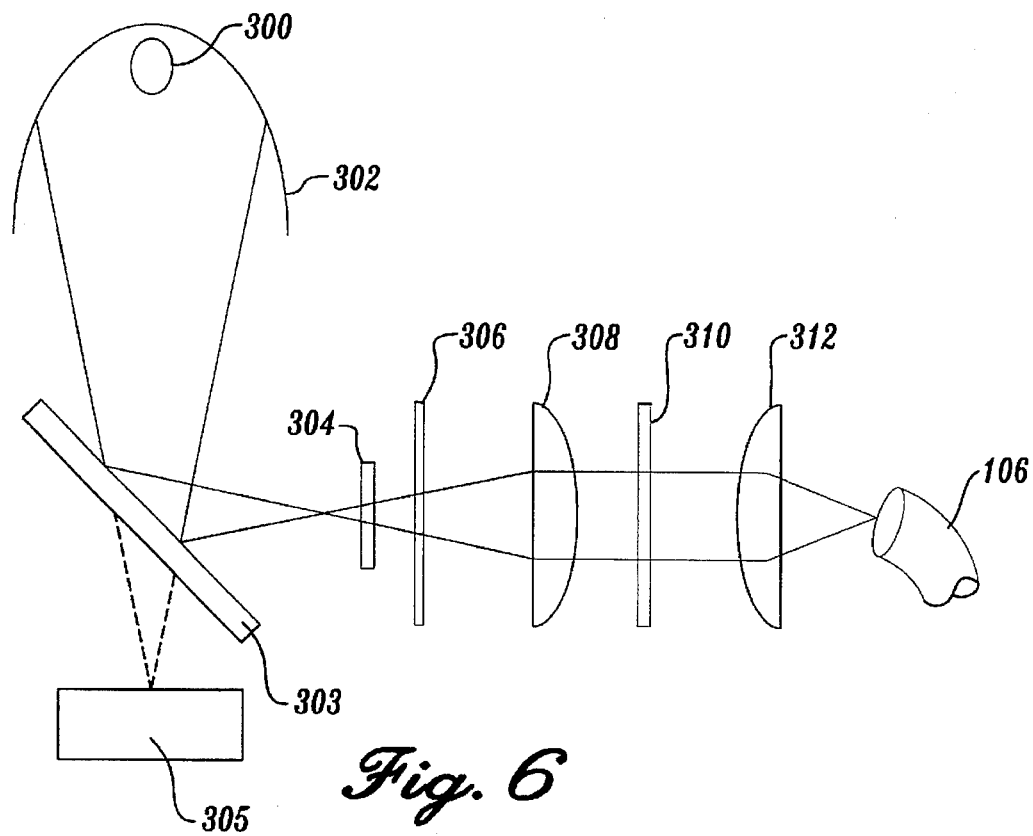
FIG. 6 is a diagram of an excitation light source according to another aspect of the present invention.

FIG. 6 is a schematic diagram of the excitation light source 100 shown in FIG. 1. The light source 100 produces an intense blue light at the 436 nanometer mercury atomic line that is used to illuminate large internal body cavities. The light source includes a one hundred watt mercury arc lamp 300 that produces light having a significant blue spectral content. The inventors have found that in order to couple the blue light produced by the lamp 300 into the illumination guide 106 of the endoscope, the arc size of the lamp must be smaller than the diameter of the illumination guide of the endoscope. In the preferred embodiment of the invention, the arc lamp used is an Ushio model number USH-102D having arc dimensions of approximately 0.25 millimeters.

Surrounding the arc lamp 300 is a collecting mirror 302, which in the present embodiment of the invention is elliptical in shape. The arc lamp 300 is positioned at one foci of the mirror 302 so that light from the sides and rear of the lamp 300 is gathered by the mirror and directed towards a dichroic mirror 303. In this way, as much as 80% of the radiation energy of the lamp is collected. The dichroic mirror 303 is preferably mounted below the arc lamp 300 at a position closer than the second foci of the elliptical mirror. Light having wavelengths between 350 and 450 nanometers is reflected at forty-five degrees from the face of the dichroic mirror 303 and through a 399 nanometer, low fluorescence, long pass filter 306. In addition to reflecting light in the desired spectral band, the dichroic mirror 303 also serves to pass longer wavelengths of light to a beam stop 305 allowing one to filter out the infrared radiation so that components of the light source do not suffer thermal damage. A shutter 304 positioned between the dichroic mirror 303 and a long pass filter 306 is used to control whether the excitation input is directed into the endoscope.

The long pass filter 306 attenuates the strong spectral lines produced by the mercury arc lamp in the ultraviolet range so that a coating on an interference bandpass filter 310 described below is protected from damage. After passing through the long pass filter 306, the light is directed to a one hundred millimeter focal length plano convex lens 308 that creates an optically homogenous, substantially parallel light beam, which is necessary for high out-of-band rejection filtering by a color filter 310.

The color filter, which preferably comprises an interference bandpass filter, is positioned perpendicular to the light beam produced by the lens 308 to attenuate light having wavelengths less than 400 nanometers and greater than 450 nanometers.

In the present embodiment of the invention, the dichroic mirror 303 reflects about 10% of the light outside the band of 350–450 nanometer band. Because a very pure excitation light is required for tissue fluorescence imaging, the interference bandpass filter 310 is used to further reduce the amount of light outside of the interested wavelength band (420 nanometers to 450 nanometers). The bandpass filter 310 has an out of band transmittance of smaller than $5\times10^{-5}$ so that light with wavelengths less than 420 nanometers or greater than 450 nanometers is weaker than the autofluorescence light emitted from the tissue.

After passing through the interference bandpass filter 310, the remaining light is directed to a 65 millimeter focal length lens 312 that focuses the light onto an end of the illumination guide 106 (FIG. 3).

The light source 100 shown in FIG. 6 provides approximately 500 milliwatts of blue light into the illumination guide of the endoscope. This light is sufficient to illuminate large internal body cavities such as the stomach or colon. The light source delivers approximately 50–80 milliwatts of excitation light at the end of the endoscope in contrast to the 15 milliwatts that are typically delivered with a laser light source. In addition, the light source 100 is easier to manufacture and maintain than a laser.

Figure 7:
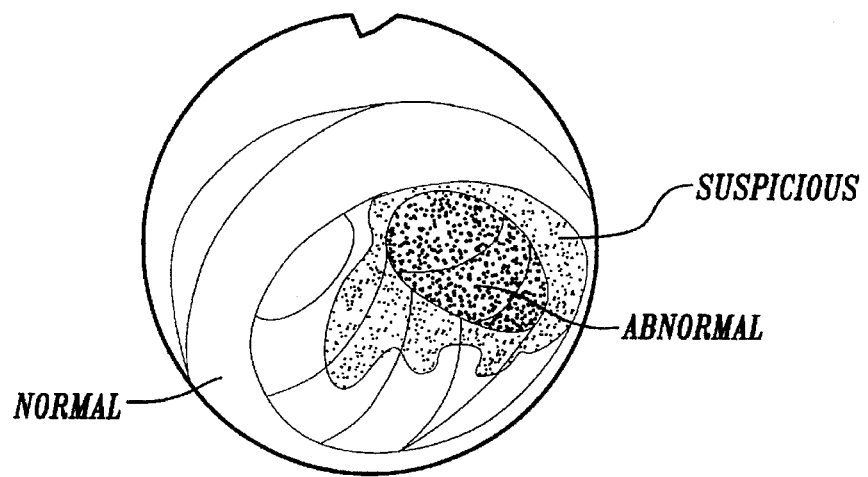
FIG. 7 is a pictorial diagram of an image produced by the cancer detection system of the present invention.

FIG. 7 is a pictorial representation of an image produced by the cancer detection system of the present invention. As indicated above, the video monitor 150 produces a color display, wherein healthy tissue appears cyan (white-blue) in color and potentially cancerous or precancerous lesions appear reddish brown. The video display produced thereby allows physicians to readily detect the presence of cancerous or precancerous lesions without the use of photosensitive drugs. In addition, the color display retains the contextual information of the tissue, thereby allowing the physician to interpret subtleties in the image that are traditionally lost in digital camera systems that employ significant digital signal processing. The cancer detection system of the present invention is ideally suited for cancer screening applications whereby it is desired to test as many patients as possible for the presence of abnormal tissue without need to administer photosensitive drugs.

While the preferred embodiment of the invention has been illustrated and described, it will be appreciated that various changes can be made therein without departing from the spirit and scope of the invention. It is therefore intended that the scope of the invention be determined solely from the following claims.

The embodiments of the invention in which an exclusive property or privilege is claimed are defined as follows:

1. A system for examining tissue to detect the presence of cancerous or precancerous tissue, comprising:

an endoscope;

a substantially monochromatic light source for producing excitation light at an excitation wavelength that will cause the tissue under examination to produce autofluorescence light, the light source including:

a) a lamp that produces excitation light;

b) a collecting mirror positioned about the lamp for collecting the excitation light produced by the lamp and directing the excitation light outwardly of the collecting mirror, c) a first dichroic mirror positioned to receive the excitation light collected by the collecting mirror and to filter the excitation light;

d) a first lens positioned to receive the filtered excitation light reflected from the first dichroic mirror in order to produce a substantially parallel beam of excitation light;

e) a color filter positioned to receive the parallel beam of excitation light, the color filter operating to filter light having wavelengths not at the excitation wavelength from the parallel beam of excitation light; and f) a second lens positioned to receive the filtered beam of excitation light that has passed through the color filter, the second lens focusing the excitation light into the endoscope in order to excite the tissue under examination;

collecting means for gathering reflected excitation light and autofluorescence light produced by the tissue under examination;

a second dichroic mirror positioned to receive the gathered, reflected excitation light and the autofluorescence light, the second dichroic mirror dividing the autofluorescence light into a first beam having wavelengths where an intensity of the autofluorescence light for abnormal tissue is substantially different from normal tissue and a second beam where an intensity of the autofluorescence light for abnormal tissue is substantially the same as normal tissue;

a first and second camera for producing a first and second autofluorescence image signal of the tissue under examination; the first camera receiving the first beam of autofluorescence light and the second camera receiving the second beam of autofluorescence light; and a color monitor having color video inputs, wherein the first autofluorescence image signal is coupled to a first color video input and the second autofluorescence image signal is coupled to another of the color video inputs, the color monitor producing a false color display whereby normal tissue and abnormal tissue appear as contrasting colors on the color monitor.

2. The system of claim 1, wherein the lamp is a mercury arc lamp.

3. The system of claim 2, wherein the collecting mirror is an elliptical mirror positioned so that the mercury arc lamp is at a foci of the elliptical mirror.

4. The system of claim 2, wherein the excitation wavelength is 436 nanometers and the first dichroic mirror reflects excitation light having wavelengths between 350 and 450 nanometers.

5. The system of claim 1, wherein the color filter is an interference bandpass filter that passes excitation light having wavelengths between 420 and 450 nanometers.

6. The system of claim 1, further comprising a second bandpass disposed between the second dichroic mirror and the first camera, the second bandpass filter passing autofluorescence light having wavelengths between 490 and 560 nanometers.

7. The system of claim 1, further comprising a red long pass filter disposed between the second dichroic mirror and the second camera, the long pass filter having a cutoff wavelength of 630 nanometers.

8. The system of claim 1, wherein each of the autofluorescence image signals has a gain, the system further comprising a control for adjusting the gain of one of the first or second autofluorescence signals produced by the first or second cameras, as a function of the gain of the other of the first or second autofluorescence image signals.

9. The system of claim 1, wherein the color monitor is an RGB monitor having red, green and blue color video inputs.

10. The system of claim 1, wherein the first and second cameras are image intensified CCD cameras.

11. Apparatus for imaging diseases in tissue using autofluorescence comprising:

a light source for generating excitation light that will cause tissue to generate characteristic autofluorescence light;

means for illuminating tissue with the excitation light thereby exciting tissue to emit said characteristic autofluorescence light;

collecting means for gathering reflected excitation light and said characteristic emitted autofluorescence light produced by the tissue;

a dichroic mirror positioned to receive the reflected excitation light and the emitted autofluorescence light collected by the collecting means, the dichroic mirror operating to separate the spectral components of said autofluorescence light into at least a first spectral band including the reflected excitation light and emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from the light within the first spectral band;

a second optical filter positioned to receive the light within the second spectral band;

a first image intensified CCD camera for receiving the autofluorescence light within the first spectral band and for producing a first autofluorescence image signal of the tissue;

a second image intensified CCD camera for receiving the autofluorescence light within the second spectral band and for producing a second autofluorescence image signal of the tissue;

a control for adjusting the gain of one of the first or second autofluorescence image signals produced by the intensified CCD cameras as a function of the gain of the other of the first or second autofluorescence image signals; and a color monitor having at least a first and a second color input, whereby the first color input is coupled to receive the first autofluorescence image signal and the second color input is coupled to receive the second autofluorescence image signal to create a combined, display image in which said abnormal and normal tissue are displayed on the color monitor.

12. The system of claim 11, further comprising a control for adjusting the function by which the gain of the first or second autofluorescence image signal is dependent on the gain of the other of the first or second autofluorescence image signal.

13. A system for detecting cancerous or precancerous tissue comprising:

a substantially monochromatic light source for producing excitation light that causes tissue under examination to produce autofluorescence light;

an endoscope positioned to receive the excitation light and to direct the excitation light into an internal body cavity of a patient and onto the tissue under examination;

means for collecting the autofluorescence light produced by the tissue under examination;

a beam splitter for dividing the collected autofluorescence light into a first beam having wavelengths where an intensity of the autofluorescence light from abnormal tissue is substantially different than from normal tissue and a second beam having wavelengths where an intensity of the autofluorescence light from abnormal tissue is substantially the same as from normal tissue;

a first and second image intensified or non-intensified CCD camera for receiving the first and second beams of autofluorescence light, respectively, the first and second image intensified or non-intensified CCD cameras producing a first and second autofluorescence image signal; and a color monitor having a red, blue and green color input, the red color input being connected to receive one of the first or second autofluorescence image signals and the blue and green color inputs are connected to receive the other of the first or second autofluorescence image signals in order to produce a display having a color that is representative of a ratio of a magnitude of the first autofluorescence signal and the second autofluorescence signal, said display providing an indication of whether the tissue is normal or abnormal.

* * * * *